(12) United States Patent
Zacharopoulos

(10) Patent No.: US 11,850,450 B2
(45) Date of Patent: Dec. 26, 2023

(54) RADIATION BEAM ALIGNMENT FOR MEDICAL LINEAR ACCELERATORS

(71) Applicant: Aktina Corp., Congers, NY (US)

(72) Inventor: Nicholas G. Zacharopoulos, West Nyack, NY (US)

(73) Assignee: Aktina Corp., Congers, NY (US)

(*) Notice: Subject to any disclaimer, the term of this patent is extended or adjusted under 35 U.S.C. 154(b) by 51 days.

(21) Appl. No.: 17/741,019

(22) Filed: May 10, 2022

(65) Prior Publication Data

US 2022/0355131 A1 Nov. 10, 2022

Related U.S. Application Data

(60) Provisional application No. 63/186,498, filed on May 10, 2021.

(51) Int. Cl.
*A61N 5/10* (2006.01)

(52) U.S. Cl.
CPC ......... *A61N 5/1081* (2013.01); *A61N 5/1049* (2013.01); *A61N 5/1067* (2013.01); *A61N 5/1075* (2013.01)

(58) Field of Classification Search
None
See application file for complete search history.

(56) References Cited

U.S. PATENT DOCUMENTS 9,192,784 B1 * 11/2015 Ritt ..................... G06T 11/005
2011/0163243 A1 7/2011 Iwata (Continued)

FOREIGN PATENT DOCUMENTS

EP 3202458 A2 8/2017
EP 3960236 A1 3/2022
(Continued)

OTHER PUBLICATIONS

Pejman Rowshanfarzad et al., "Isocenter verification for linac-based stereotactic radiation therapy: review of principles and techniques", Journal of Applied Clinical Medical Physics, vol. 12, No. 4, 2011, 10 pages.

(Continued)

*Primary Examiner* — Hoon K Song
(74) *Attorney, Agent, or Firm* — Rothwell, Figg, Ernst & Manbeck, P.C.

(57) ABSTRACT

Radiation beam alignment for a LINAC including (1) for each beam alignment parameter value of a set: (a) with a beam alignment parameter of a LINAC set to the beam alignment parameter value, using a gantry to generate a radiation beam; (b) using an imaging device to acquire a radiation transmission image indicative of a radiation field of the radiation beam after passing by a radiation opaque marker; (c) determining a location of a beam axis of the radiation beam and a center of a shadow of the marker based on the radiation transmission image; and (d) determining a target-to-beam-axis distance between the location of the beam axis and the center of the shadow of the radiation opaque marker; and (2) determining an optimum beam alignment parameter value based on the beam alignment parameter values and the target-to-beam-axis distances determined with the LINAC set to the beam alignment parameter values.

20 Claims, 14 Drawing Sheets

(56) References Cited

U.S. PATENT DOCUMENTS

2015/0093011 A1* 4/2015 Gaudio ............... A61N 5/1075
382/132
2018/0250531 A1 9/2018 Ansorge et al.

FOREIGN PATENT DOCUMENTS

| JP | 2018-33482 A | 3/2018 |
| WO | 2013/167733 A1 | 11/2013 |

OTHER PUBLICATIONS

Tarraf Torfeh et al., "Digital phantoms for the evaluation of a software used for an automatic analysis of the Winston-Lutz test in image guided radiation therapy", Retrieved from the Internet: URL:https://hal.archives-ouvertes.fr/hal-00326648/document, 2008, 12 pages.

* cited by examiner

RADIATION BEAM ALIGNMENT FOR MEDICAL LINEAR ACCELERATORS

CROSS-REFERENCE TO RELATED APPLICATION

The present application claims the benefit of priority to U.S. Provisional Patent Application Ser. No. 63/186,498, filed on May 10, 2021, which is incorporated herein by reference in its entirety.

BACKGROUND

Field of Invention

The present invention relates generally to radiation therapy in which a medical linear accelerator (LINAC) delivers a radiation beam to a precise point within a patient. In particular, the present invention relates to aligning the radiation beam for the medical LINAC.

Discussion of the Background

1.1. LINAC Overview

Radiation therapy is a type of cancer treatment that uses intense high energy radiation beams to kill cancer cells. FIGS. 1 and 2 illustrate a medical linear accelerator (LINAC) 100 including a gantry 102 and a couch 106. As shown in FIGS. 1 and 2, the gantry 102 includes a collimator 104. As shown in FIG. 2, the collimator 104 defines a field of a radiation beam 210 generated by the LINAC 100. During treatment, the gantry 102 of the LINAC 100 delivers the radiation beams to a precise location within a patient (not shown) supported on the couch 106. The radiation exits from the collimator 104 and enters the patient that is positioned on the treatment couch 106.

1.2 Radiation Beam

FIG. 2 is a cross-sectional view illustrating the gantry 102 of the LINAC 100 and the radiation beam 210 emitted by the LINAC 100. The radiation beam first travels up a waveguide 202 in an arm of the gantry 102 and then travels through a 270° bending magnet 204 before finally exiting the collimator 104 towards the patient. Reference numeral 206 identifies the radiation beam 210 as it travels through the bending magnet 204. The angle that the radiation beam 210 exits the collimator 104, relative to the radiation beam 210 before traveling through the bending magnet 204, is the beam bending angle 208. The beam bending angle 208 can be modified by altering the amount of current applied to the bending magnet 204.

As shown in FIG. 2, the radiation beam 210 may include a central beam axis 212, a superior beam edge 214, and an inferior beam edge 216. In some aspects, as shown in FIG. 2, the radiation beam 210 may be created in the LINAC 100 by accelerated electrons within the waveguide 202 and bending the electrons downward through an exit window.

1.3 Beam Alignment

FIG. 3 illustrates a setup used to determine whether the radiation beam 210 is aligned to a target, which may be a radiation opaque marker 320. In FIG. 3, the LINAC 100 is delivering a radiation beam 210 through a radiation opaque marker 320. An imaging device 318 of the LINAC 100 acquires a two-dimensional transmission image of the radiation beam 210 as it passes through the marker 320.

A detailed view of a marker assembly 400 including the radiation opaque marker 320 is shown in FIG. 4. In FIG. 4, a high density spherical marker 320 is connected to a low density support rod 422 that then connects to a base 423. The base 423 is set on a top of the couch 106 so that the marker 320 can be positioned.

The radiation beam 210 can be considered aligned to the target 320 when the target 320 is centered within the radiation field of the radiation beam 210. An example of this is shown in FIG. 5. In FIG. 5, radiation emanates from a source 524 of the gantry 102 and travels through a collimator 104, which is composed of left side and right side high-density beam attenuators 104a and 104b. The opening at the center of the collimator 104 defines the radiation field that will reach the patient. The radiation field edges 214 and 216 created by the collimator 104 are shown in dashed lines in FIG. 5. The radiation field edges 214 and 216 project onto the imaging panel 318 at locations 526 and 528, respectively. The locations 526 and 528 of the radiation field edges 214 and 216 can be determined by imaging processing techniques. The position of the target 320 will also project onto the imaging plane (at location 530), and the distance of the projected target position 530 relative to the field center can be computed. In this example, the radiation beam 210 is considered aligned if the lateral distances from the target 320 to the field edges 214 and 216 on the left and right sides are equal (i.e., d1=d2).

FIG. 6 shows a typical image 600 (e.g., an EPID image) through the marker 320. In FIG. 6, the dark square region 602 is created by a square radiation field of the radiation beam 210 exposing the imaging device 318, and the lighter inner circular shape 604 is created by the shadow of the radiation opaque marker 320 that is located within the radiation field. The images are analyzed using image processing techniques to find the centers of the field and the marker 320 in each image (an example of an image 700 with the determined field and marker locations 702 and 704 is shown in FIG. 7).

1.4 Choice of Target Location

As shown in FIG. 8, the gantry 102 may be capable of rotating a full 360° around the patient so as to optimize the entry of the radiation beam 210 into the patient. As shown in FIG. 8, the gantry 102 may rotate about a gantry axis of rotation 808. As shown in FIG. 9, at any of the angle of the gantry 102, the collimator 104 may rotate about a collimator axis of rotation 910. The collimator 104 may be capable of rotating a full 360°.

As described above, an aligned beam 210 is one that is centered about a target 320. The choice of target location depends on the goal of beam alignment. Two types of beam are collimator axis alignment and isocenter alignment.

Collimator axis alignment ensures that the radiation beam 210 stays aligned with the collimator axis of rotation 910 as the gantry 102 rotates. In this case, the target 320 is positioned on the collimator axis of rotation 910 for any gantry angle. The beam bending magnet currents are adjusted to ensure that the beam 210 is aligned to this target 320.

Isocenter beam alignment ensures that the beam 210 is aligned to a target 320 that remains at a fixed point in space (usually the LINAC isocenter). The gantry 102 typically undergoes mechanical errors as it rotates, which results in the blurring of the radiation field. By carefully adjusting the beam bending magnetic currents to maintain the alignment on a fixed point in space, no matter what gantry rotation errors are incurred, the mechanical errors due to gantry rotation can be minimized or eliminated.

SUMMARY

One aspect of the invention may provide a method including, for each beam alignment parameter value of a set of beam alignment parameter values: (i) with a beam alignment parameter of a linear accelerator (LINAC) set to the beam alignment parameter value, using a gantry of the LINAC to generate a radiation beam; (ii) using an imaging device of the LINAC to acquire a radiation transmission image indicative of a radiation field of the radiation beam after passing by a radiation opaque marker; (iii) determining a location of a beam axis of the radiation beam and a center of a shadow of the radiation opaque marker in the radiation field of the radiation beam based on the radiation transmission image; and (iv) determining a target-to-beam-axis distance between the location of the beam axis of the radiation beam and the center of the shadow of the radiation opaque marker in the radiation field of the radiation beam. The method may include determining an optimum beam alignment parameter value based on the beam alignment parameter values of the set of beam alignment parameter values and the target-to-beam-axis distances determined with the LINAC set to the beam alignment parameter values of the set of beam alignment parameter values.

In some aspects, the method may further include, for each beam alignment parameter value of the set of beam alignment parameter values, setting the beam alignment parameter of the LINAC to the beam alignment parameter value. In some aspects, the beam alignment parameter of the LINAC may be an amount of current applied to a bending magnet of the LINAC. In some aspects, the optimum beam alignment parameter value may be determined such that a target-to-beam-axis distance between a location of a beam axis of a radiation beam generated by the LINAC with the beam alignment parameter set to the optimum beam alignment parameter value and a center of a shadow of the radiation opaque marker in the radiation field of the radiation beam generated by the LINAC with the beam alignment parameter set to the optimum beam alignment parameter value would be zero.

In some aspects, determining the optimum beam alignment parameter value may include determining a function that models a dependence of the target-to-beam-axis distance on the beam alignment parameter based on the beam alignment parameter values of the set of beam alignment parameter values and the target-to-beam-axis distances determined with the LINAC set to the beam alignment parameter values of the set of beam alignment parameter values. In some aspects, determining the optimum beam alignment parameter value may include using the function to determine a beam alignment parameter value at which a target-to-beam-axis distance would be zero. In some aspects, the function may be a first degree polynomial function. In some aspects, determining the function may include performing a linear least square fit for the target-to-beam-axis distances determined with the LINAC set to the beam alignment parameter values of the set of beam alignment parameter values.

In some aspects, the method may further include setting the beam alignment parameter of the LINAC to the optimum beam alignment parameter value and, with the beam alignment parameter of the LINAC set to the optimum beam alignment parameter value, using the LINAC to generate a radiation beam.

In some aspects, determining the location of the beam axis of the radiation beam may include determining a center of the radiation field of the radiation beam based on the radiation transmission image, and the determined location of the beam axis of the radiation beam may be the determined center of the radiation field of the radiation beam.

In some aspects, determining the location of the beam axis of the radiation beam may include determining a first center of the radiation field of the radiation beam based on the radiation transmission image. In some aspects, determining the location of the beam axis of the radiation beam may include rotating a collimator of the LINAC by 180 degrees. In some aspects, determining the location of the beam axis of the radiation beam may include using the imaging device of the LINAC to acquire a second radiation transmission image indicative of the radiation field of the radiation beam with the collimator rotated by 180 degrees. In some aspects, determining the location of the beam axis of the radiation beam may include determining a second center of the radiation field of the radiation beam based on the second radiation transmission image. In some aspects, determining the location of the beam axis of the radiation beam may include averaging the first and second centers, and the determined location of the beam axis of the radiation beam may be the average of the first and second centers.

In some aspects, the radiation opaque marker may be positioned in the radiation field of the radiation beam at an axis of rotation of a collimator of the gantry of the LINAC for one or more gantry angles. In some alternative aspects, the radiation opaque marker may be positioned in the radiation field of the radiation beam at an isocenter of the LINAC.

Another aspect of the invention may provide an apparatus. The apparatus may be configured to, for each beam alignment parameter value of a set of beam alignment parameter values: (i) with a beam alignment parameter of the a linear accelerator (LINAC) set to the beam alignment parameter value, use a gantry of the LINAC to generate a radiation beam; (ii) use an imaging device of the LINAC to acquire a radiation transmission image indicative of a radiation field of the radiation beam after passing by a radiation opaque marker; (iii) determine a location of the beam axis of the radiation beam and a center of a shadow of the radiation opaque marker in the radiation field of the radiation beam based on the radiation transmission image; and (iv) determine a target-to-beam-axis distance between the location of the beam axis of the radiation beam and the center of the shadow of the radiation opaque marker in the radiation field of the radiation beam. The apparatus may be configured to determine an optimum beam alignment parameter value based on the beam alignment parameter values of the set of beam alignment parameter values and the target-to-beam-axis distances determined with the LINAC set to the beam alignment parameter values of the set of beam alignment parameter values.

In some aspects, the apparatus may be further configured to cause the LINAC to, for each beam alignment parameter value of the set of beam alignment parameter values, set the beam alignment parameter of the LINAC to the beam alignment parameter value. In some aspects, the gantry may include a bending magnet, and the beam alignment parameter of the LINAC may be an amount of current applied to the bending magnet. In some aspects, the optimum beam alignment parameter value may be determined such that a target-to-beam-axis distance between a location of a beam axis of a radiation beam generated by the LINAC with the beam alignment parameter set to the optimum beam alignment parameter value and a center of a shadow of the radiation opaque marker in the radiation field of the radiation beam generated by the LINAC with the beam alignment parameter set to the optimum beam alignment parameter value would be zero.

In some aspects, the apparatus may be configured to, in determining the optimum beam alignment parameter value, determine a function that models a dependence of the target-to-beam-axis distance on the beam alignment parameter based on the beam alignment parameter values of the set of beam alignment parameter values and the target-to-beam-axis distances determined with the LINAC set to the beam alignment parameter values of the set of beam alignment parameter values. In some aspects, the apparatus may be configured to, in determining the optimum beam alignment parameter value, use the function to determine a beam alignment parameter value at which a target-to-beam-axis distance would be zero. In some aspects, the function may be a first degree polynomial function. In some aspects, the apparatus may be configured to, in determining the function, perform a linear least square fit for the target-to-axis-beam distances determined with the LINAC set to the beam alignment parameter values of the set of beam alignment parameter values.

In some aspects, the apparatus is further configured to set the beam alignment parameter of the LINAC to the optimum beam alignment parameter value and, with the beam alignment parameter of the LINAC set to the optimum beam alignment parameter value, use the LINAC to generate a radiation beam. In some aspects, the gantry may include a collimator and a bending magnet.

In some aspects, in determining the location of the beam axis of the radiation beam, the apparatus may be configured to determine a center of the radiation field of the radiation beam based on the radiation transmission image, and the determined location of the beam axis of the radiation beam may be the determined center of the radiation field of the radiation beam.

In some alternative aspects, in determining the location of the beam axis of the radiation beam, the apparatus may be configured to: (i) determine a first center of the radiation field of the radiation beam based on the radiation transmission image; (ii) rotate a collimator of the LINAC by 180 degrees; (iii) use the imaging device of the LINAC to acquire a second radiation transmission image indicative of the radiation field of the radiation beam with the collimator rotated by 180 degrees; (iv) determine a second center of the radiation field of the radiation beam based on the second radiation transmission image; and (v) average the first and second centers, and the determined location of the beam axis of the radiation beam may be the average of the first and second centers.

Still another aspect of the invention may provide a computer program including instructions for adapting an apparatus to perform any of the methods set forth above. Yet another aspect of the invention may provide a carrier containing the computer program, and the carrier may be one of an electronic signal, optical signal, radio signal, or compute readable storage medium.

Still another aspect of the invention may provide an apparatus including processing circuitry and a memory. The memory may contain instructions executable by the processing circuitry, whereby the apparatus is operative to perform any of the methods set forth above.

Yet another aspect of the invention may provide an apparatus adapted to any of the methods set forth above.

Still another aspect of the invention may provide any combination of the aspects set forth above.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

Figure 1:
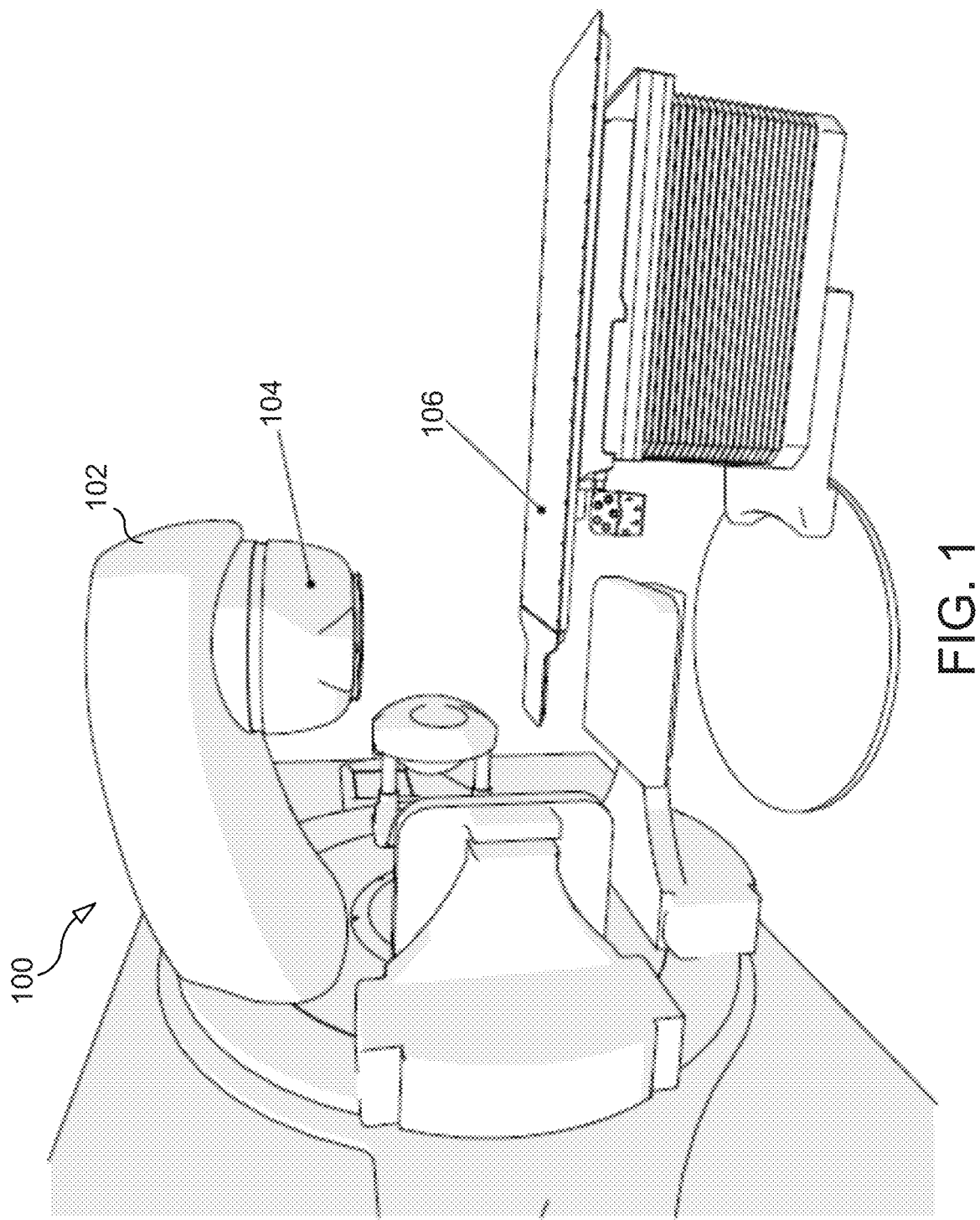
FIG. 1 illustrates a medical linear accelerator (LINAC).
Figure 2:
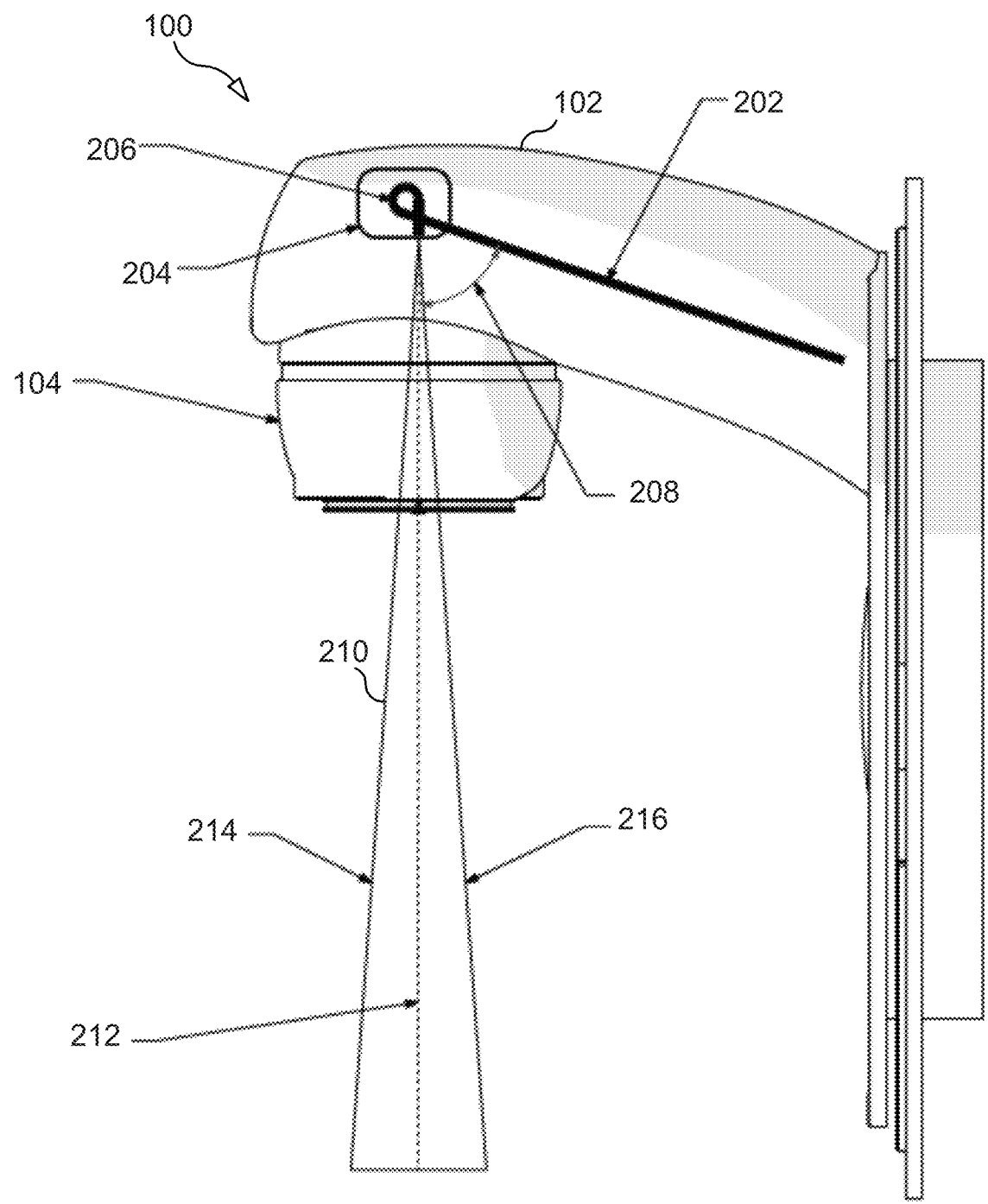
FIG. 2 is a cross-sectional view of a gantry of a LINAC and a radiation beam emitted by the LINAC according to some aspects.
Figure 3:
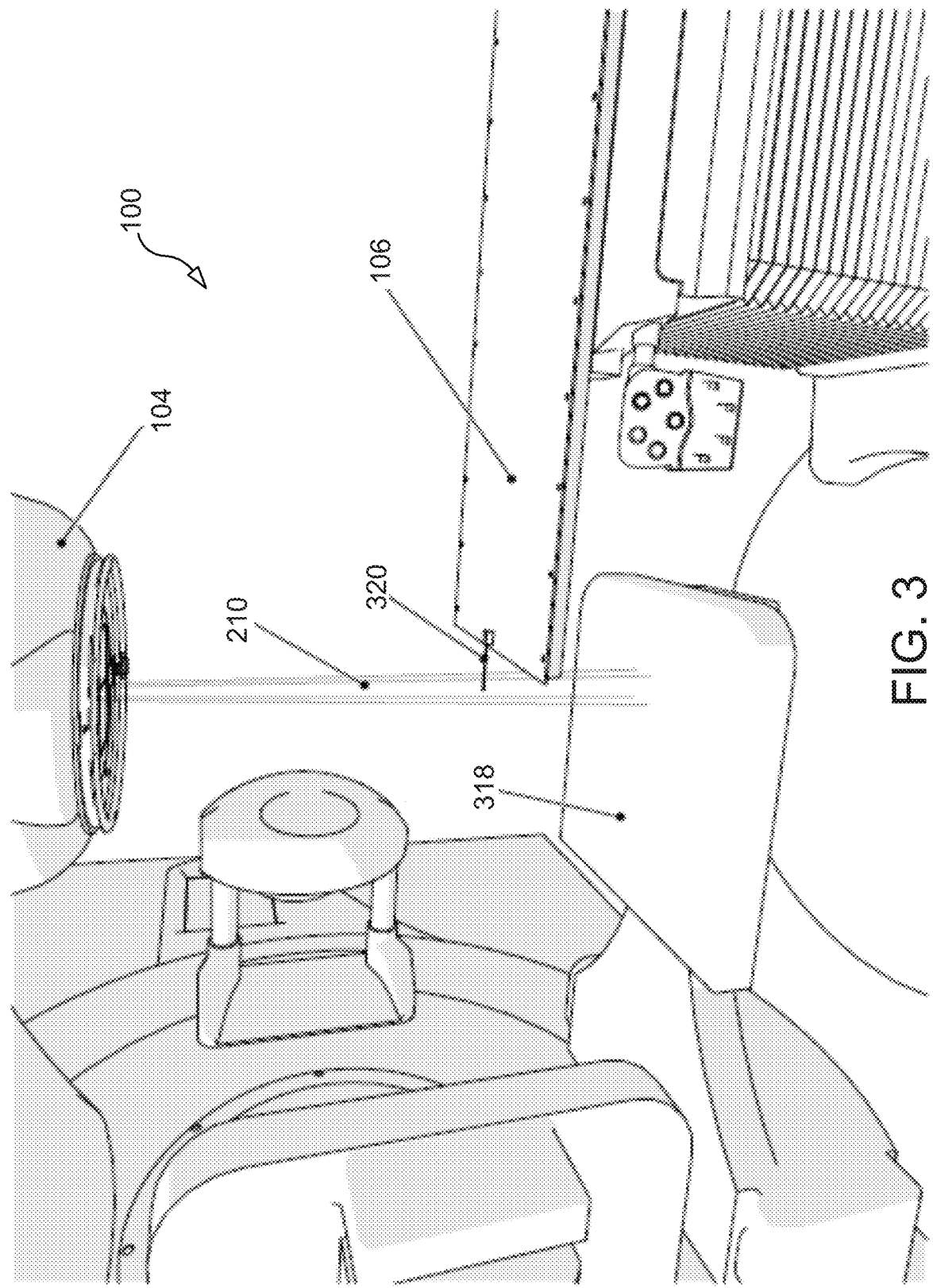
FIG. 3 illustrates a radiation beam and imaging panel of the LINAC.
Figure 4:
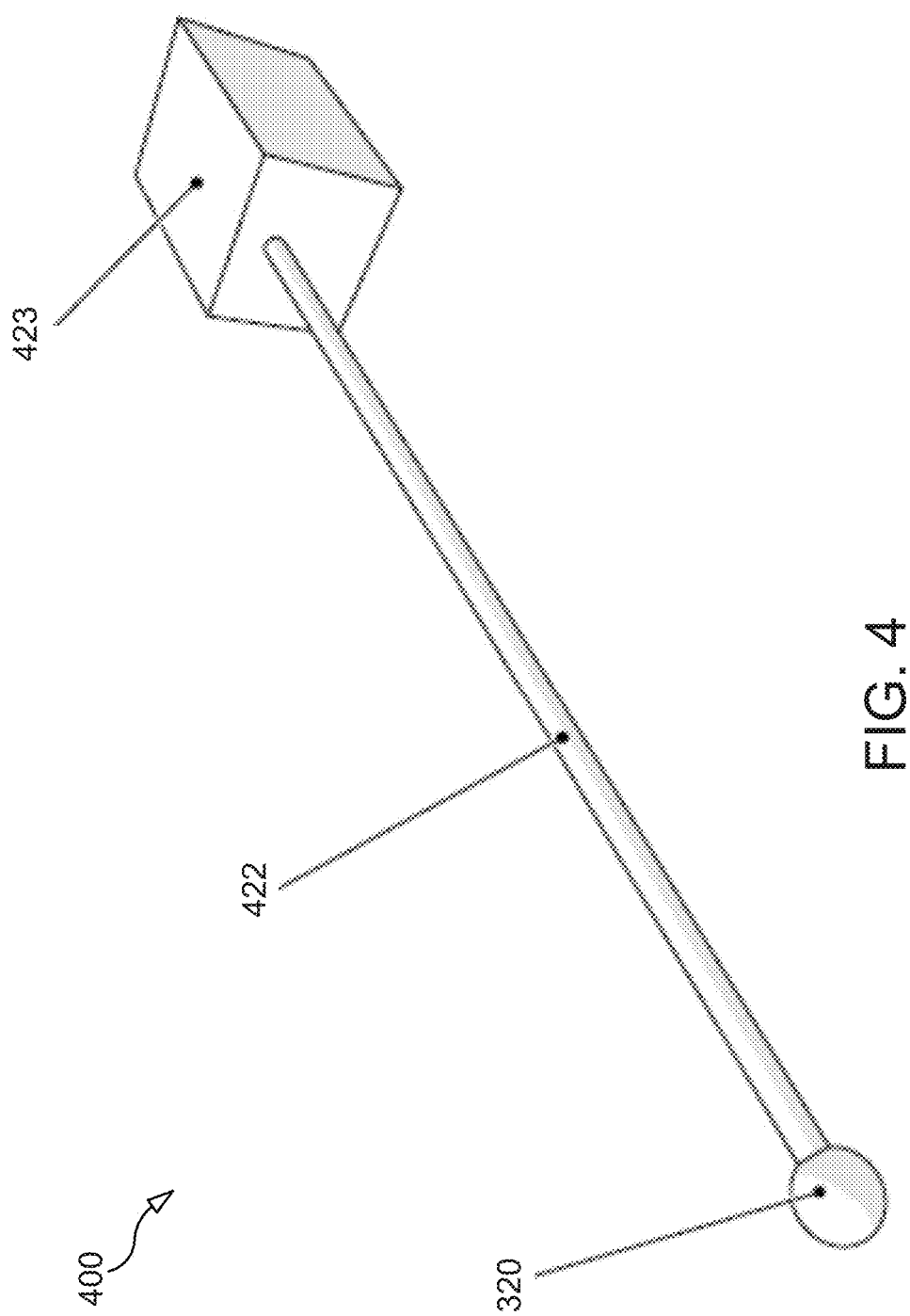
FIG. 4 illustrates a marker assembly.
Figure 5:
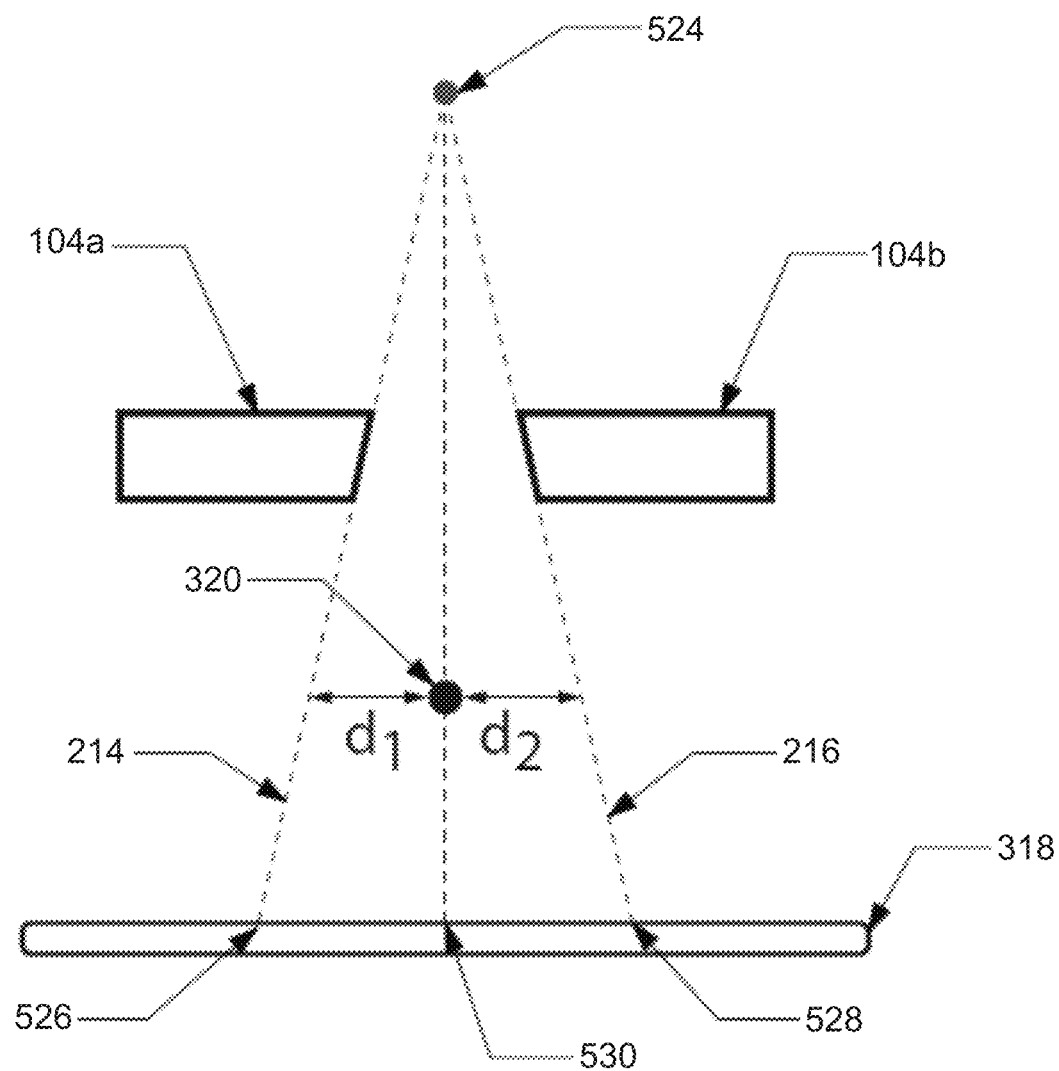
FIG. 5 illustrates a radiation beam that aligned to a target, as the target is centered within the radiation field ($d_1$-$d_2$).
Figure 6:
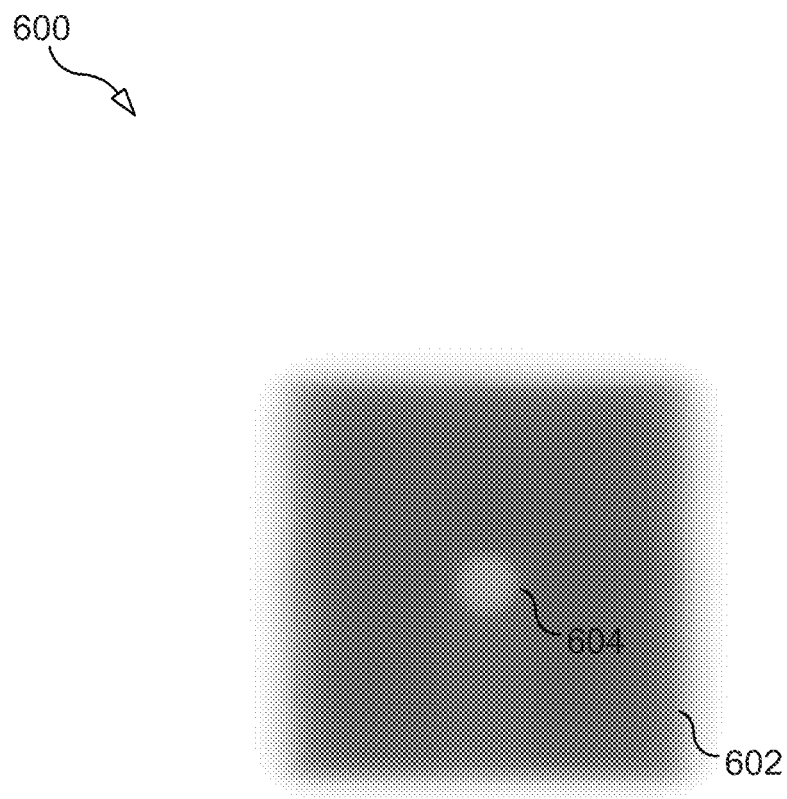
FIG. 6 illustrates an unprocessed radiation transmission image.
Figure 7:
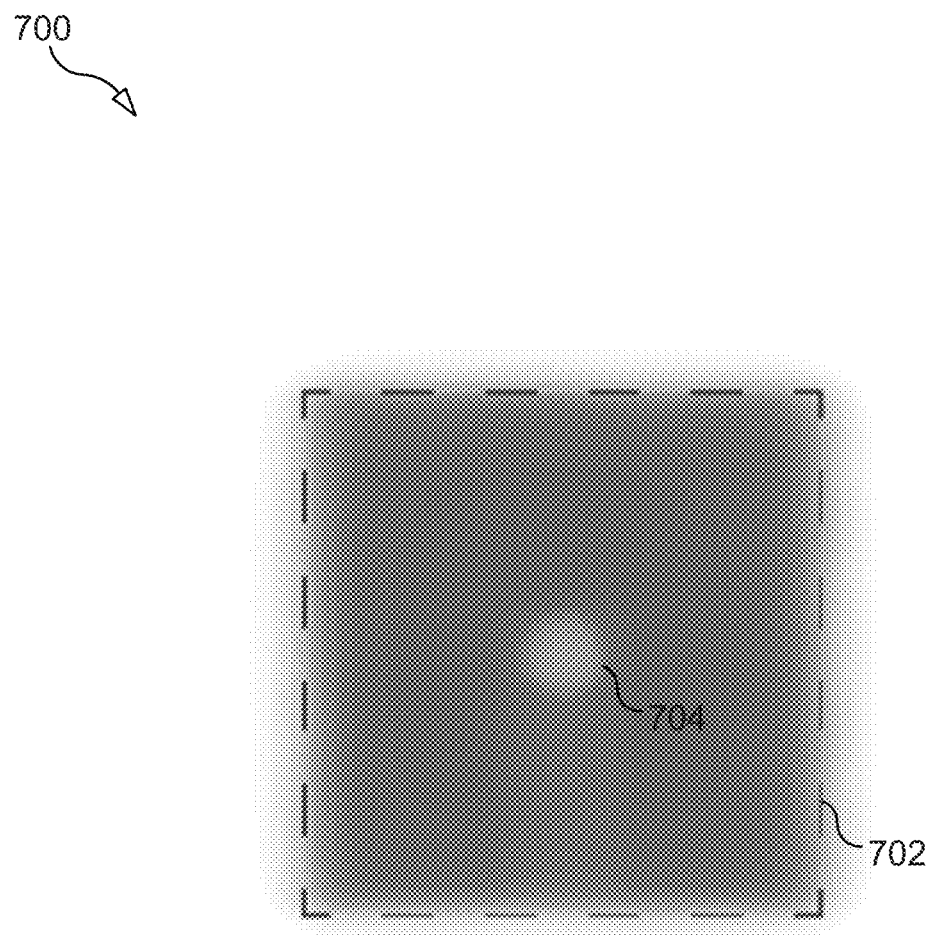
FIG. 7 illustrates a processed radiation transmission image.
Figure 8:
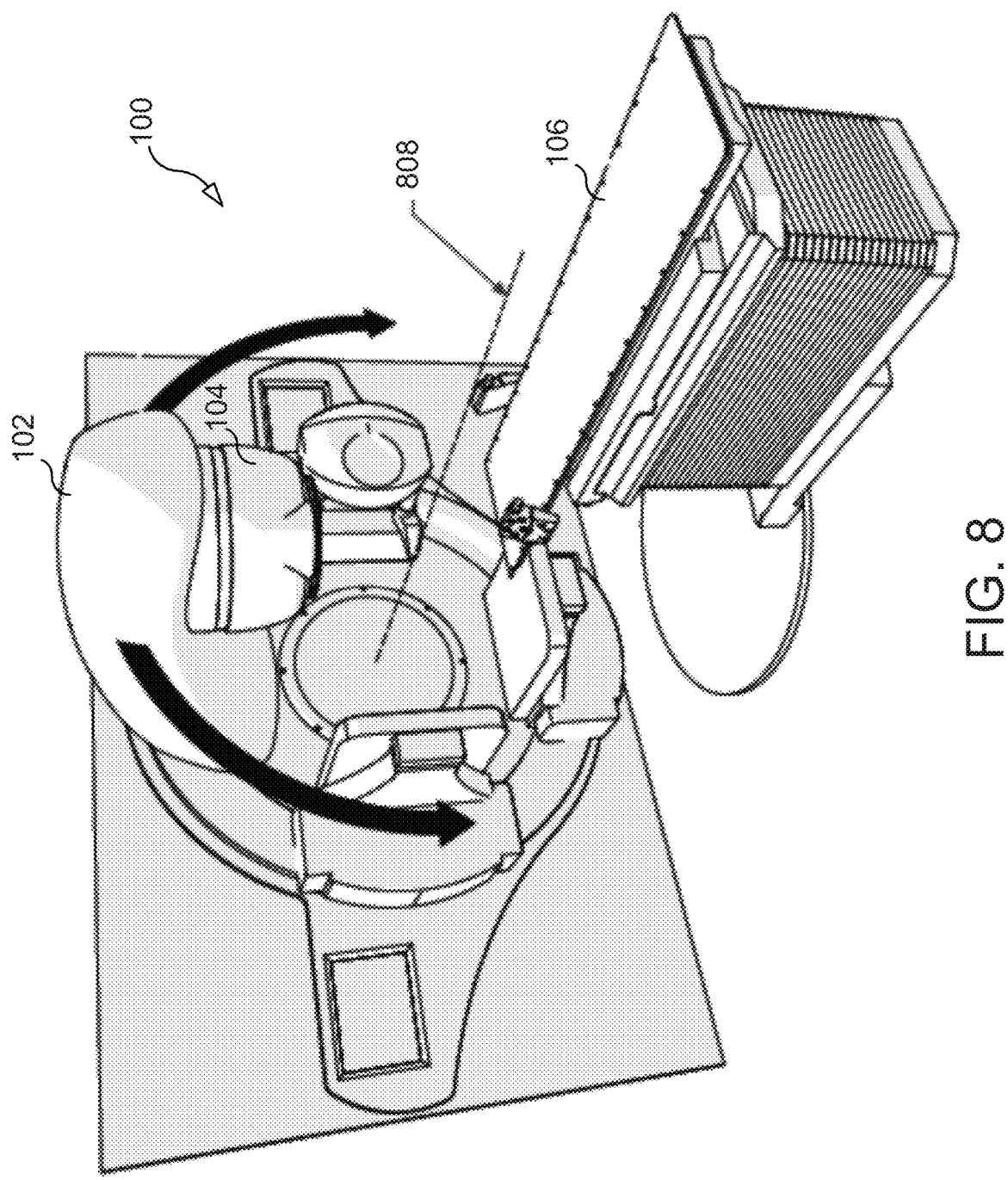
FIG. 8 illustrates rotation of a gantry of the LINAC.
Figure 9:
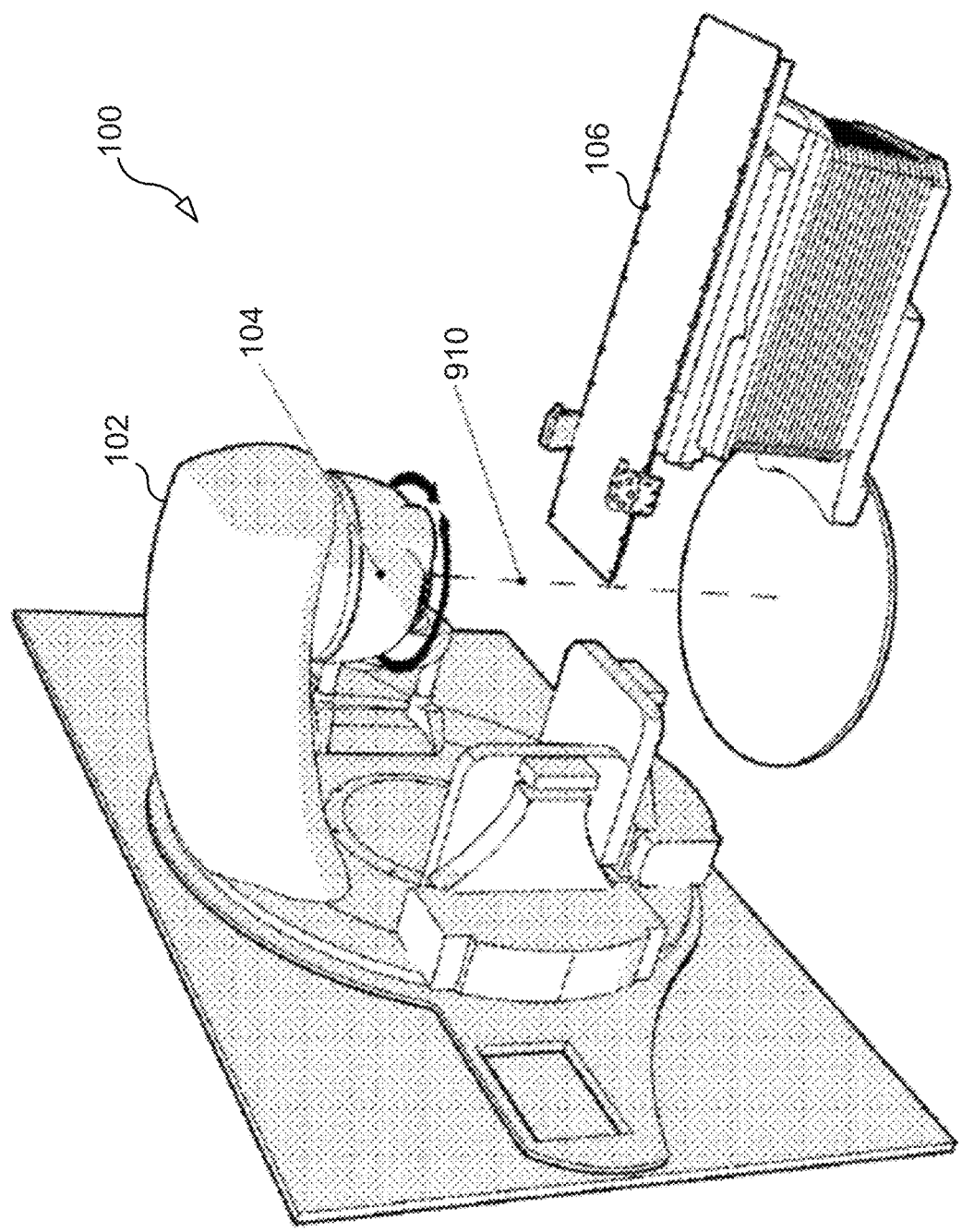
FIG. 9 illustrates rotation of a collimator of the LINAC.

DETAILED DESCRIPTION OF PREFERRED EMBODIMENTS 2.1 Definitions

In this application, the term "beam axis" can be a three-dimensional vector that represents the center of a radiation beam.

In this application, the term "collimator" can be the component (e.g., collimator 104) of the LINAC that shapes the radiation field by trimming the field with radiation-opaque attenuators (e.g., left side and right side high-density beam attenuators 104a and 104b) that can be adjusted to created arbitrary field shapes and sizes.

In this application, the term "couch" can be a component (e.g., couch 106) of a LINAC (e.g., LINAC 100) that supports the patient.

In this application, the term "gantry" may be a component (e.g., gantry 102) of a LINAC (e.g., LINAC 100) that rotates about the patient while delivering the radiation beam.

In this application, the term "imaging panel" (e.g., an electronic portal imaging device (EPID) can be a component (e.g., imaging device 318) of a LINAC (e.g., LINAC 100) that measures the x-ray intensity transmitted through a patient from a radiation port (e.g., during a treatment session). The imaging panel may, for example, convert electronically a radiation signal into a two-dimensional (2D) digital radiographic image to verify the correct beam placement in relation to the patient's anatomy.

In this application, the term "isocenter" can be the location in space that minimizes the radiation beam axis miss distance for all gantry angles.

In this application, the term "target" can be a spherical radiation-opaque marker that can visualized on a x-ray transmission image created on a LINAC.

2.2 Beam Alignment

Aspects of the invention may relate to sweeping the LINAC beam alignment through a range of values and finding an optimal value by mathematically fitting the measured target-to-field-center distance vs. the beam alignment parameter. FIGS. 10A-10D illustrate an example of incremental adjustments to the alignment of the radiation beam 210 for the purposes of aligning the radiation beam 210 to the target 320. In some aspects, the target 320 may be positioned on the axis 910 of rotation of the collimator 104 of the gantry 102 for any gantry angle. In some alternative aspects, the target 320 may be positioned at the LINAC isocenter. However, positioning the target 320 on the collimator axis of rotation 910 or at the LINAC isocenter is not required, and, in some further alternative aspects, the target 320 may be positioned at a different location (e.g., for a different goal of beam alignment than collimator axis alignment or isocenter alignment).

Figure 10A:
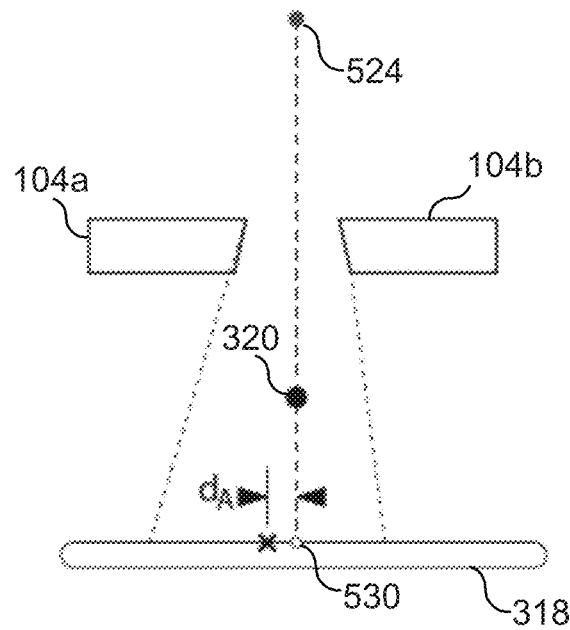
FIGS. 10A-10D illustrate an example of incremental adjustments to the alignment of the radiation beam for the purposes of aligning the beam to the target according to some aspects.
Figure 10B:
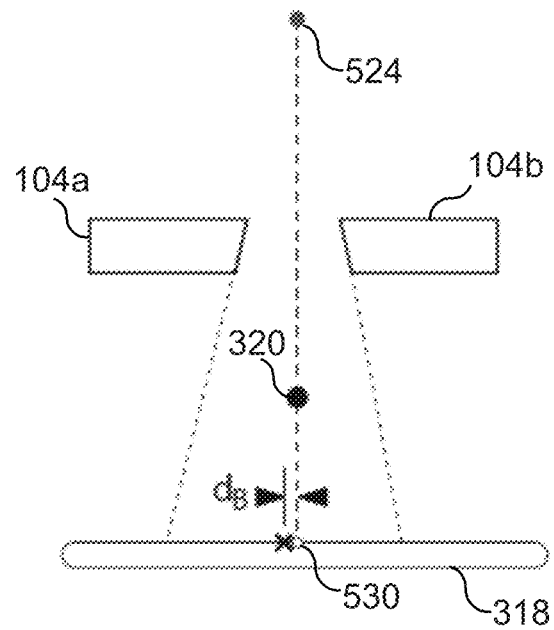
Figure 10C:
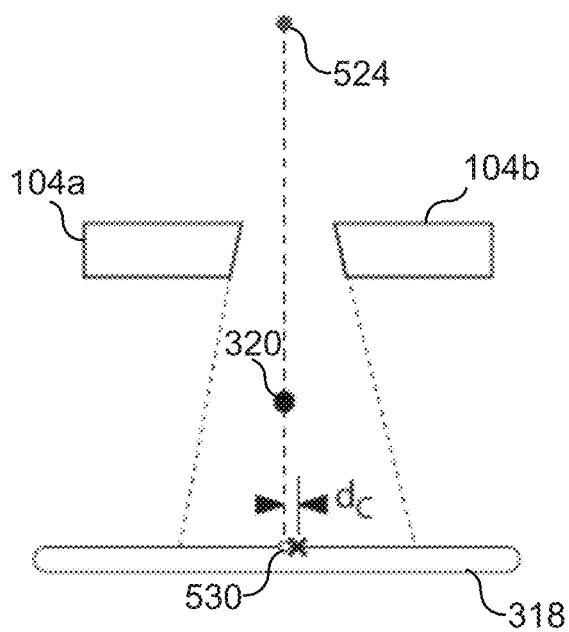
Figure 10D:
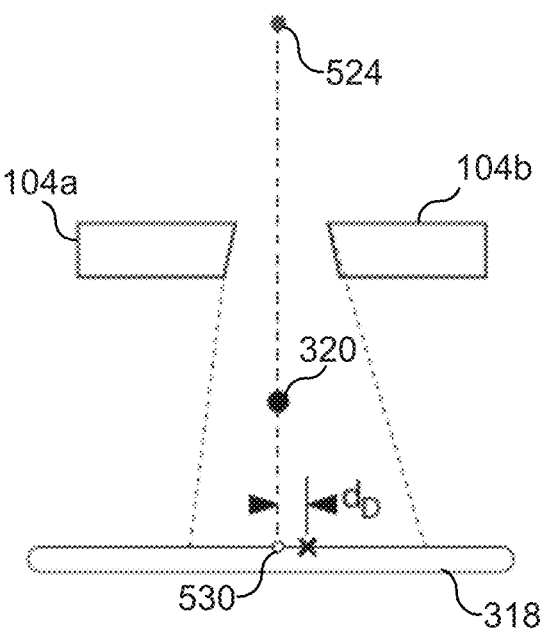

FIGS. 10A-10D represent four different increasing beam alignment parameters that result a projected radiation field moving from the left in FIG. 10A to the right in FIG. 10D on the imaging panel 318. In FIGS. 10A-10D, the X symbol represents the measured center of the radiation field of the radiation beam 210, and $d_X$ represents the distance from the center of the projected radiation field to the center of the projected target (e.g., the center of the shadow of the radiation opaque marker 320), where X is the sub-figure letter (e.g., A, B, C, or D).

2.3 Optimal Bending Parameters

Figure 11:
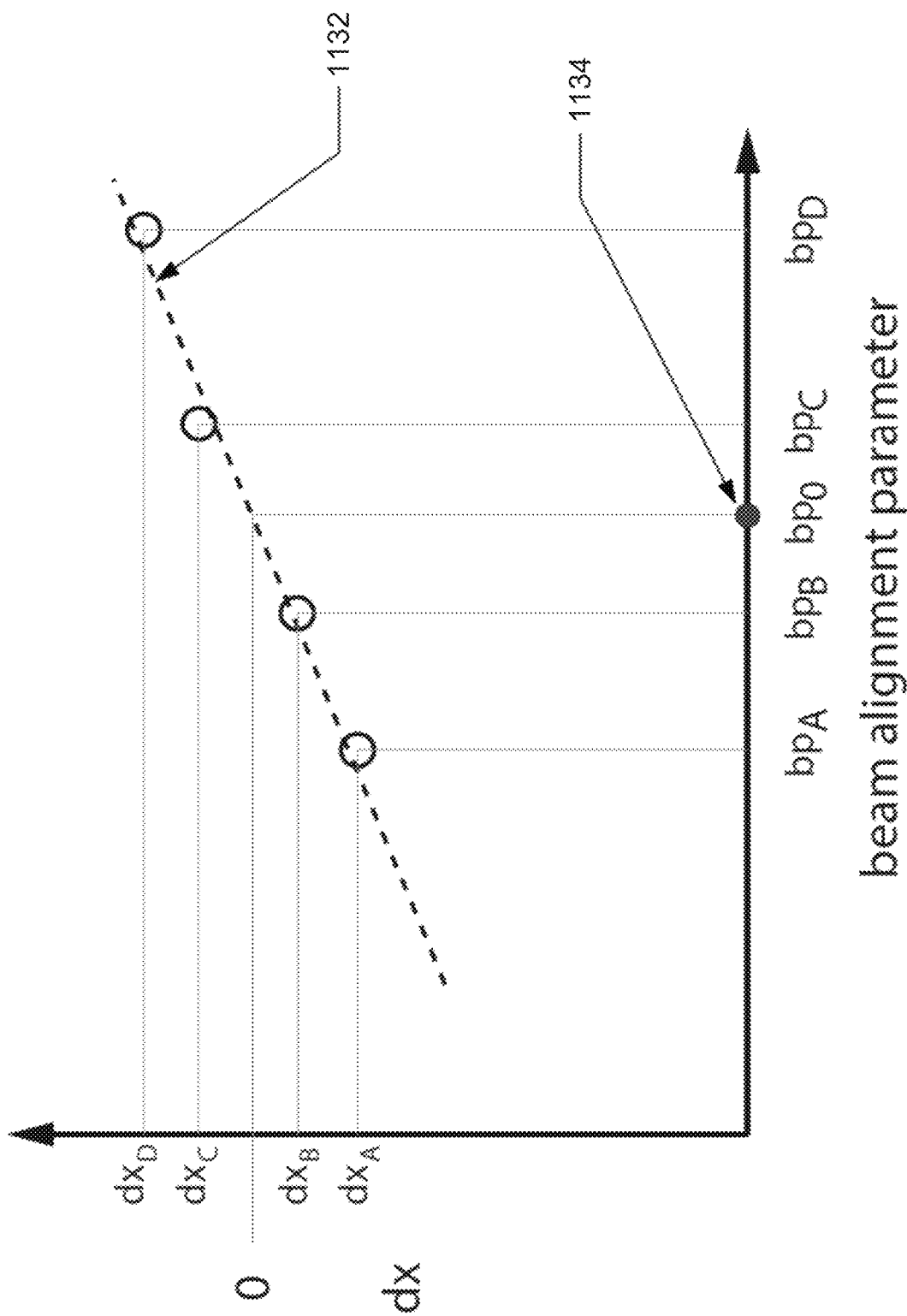
FIG. 11 illustrates determination of an optimal beam bending parameter value $b_{p0}$ that will result in a $d_x=0$ according to some aspects.

In some aspects, the optimal bending-magnet current may result in the target 320 appearing to be in the center of the projected field on the imaging panel 318. In some aspects, as shown in FIG. 11, to determine the optimal value, a linear least-square fit of the target-to-field-center distances ($d_A$ through $d_D$ in FIGS. 10A-10D, respectively) versus the beam alignment parameter used for each acquisition may be performed. In FIG. 11, $bp_A$ represents the beam alignment parameter used in FIG. 10A, which resulted in a target-to-field-center distance of $d_A$. Similarly, bpB, bpC, and bpD are the beam alignment parameters used in FIGS. 10B-10D, respectively, which resulted in target-to-field-center distances of $d_A$, $d_B$, $d_C$, respectively.

In some aspects, the linear least-squares fit 1132 may be computed, and the value $bp_0$ 1134 that yields $d_X=0$ may be computed from the fit parameters.

2.4 Implementation Example

In some aspects, a process may be carried out for radiation beam alignment of the LINAC 100 in one direction. In some aspects, the process may include a step (1) of positioning the target 320 within the radiation field of the radiation beam 210. In some aspects, the target 320 may be positioned on the collimator center of rotation or at another location (e.g., isocenter). In some aspects, the process may include a step (2) of setting the beam alignment parameter to an initial value (e.g., $bp_A$). In some aspects, the process may include a step (3) of acquiring a transmission image. In some aspects, the process may include a step (4) of altering the beam alignment parameter (e.g., to $bp_B$). In some aspects, the process may include a step (5) of acquiring another transmission image. In some aspects, the process may include a step (6) of repeating the steps (4) and (5) for the full range of the beam alignment parameters. Although four different beam alignment parameters are shown in FIGS. 10A-10D for the sake of simplicity, the full range of the beam alignment parameters is not limited to four values, and, in some alternative aspects, the full range of the beam alignment parameters may have many more (e.g., hundreds or thousands) of values.

In some aspects, the process may include a step (7) of post-processing the images to determine $d_X$ (the distance between the target position and the center of the radiation field) for each transmission image acquired. In some aspects, the process may include a step (8) of performing a least square fit for $d_X$ values vs the beam alignment parameter. In some aspects, the process may include a step (9) of using the fit parameters from step (8) to determine the beam alignment parameter $bp_0$ that yields dx=0.

In some aspects, steps (2) through (9) may be repeated for each direction that the beam can be aligned.

2.5 Flowcharts

Figure 12:
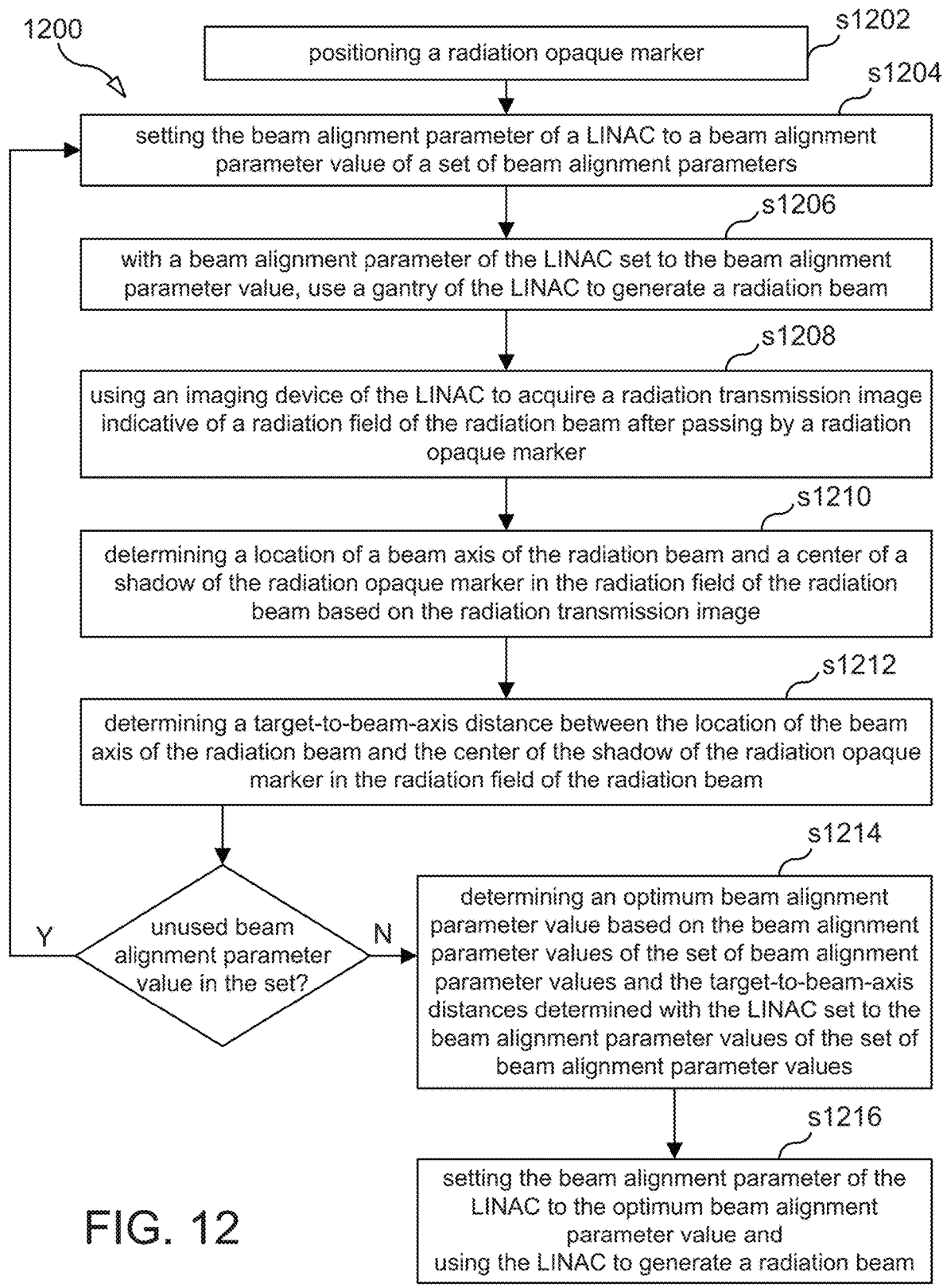
FIG. 12 illustrates a process according to some aspects.

FIG. 12 illustrates a process 1200 according to some aspects. In some aspects, one or more of the steps of the process 1200 may be performed by the LINAC 100 (e.g., the controller 1300 of the LINAC 100 shown in FIG. 13). In some aspects, one or more of the steps of the process 1200 may be additionally or alternatively be performed by an apparatus (e.g., the apparatus 1400 of FIG. 14).

In some aspects, the process 1200 may include a step 1202 of positioning a radiation opaque marker 320 (e.g., in a radiation field of the radiation beam 210). In some aspects, the radiation opaque marker 320 may be positioned by placing a base 423 of a marker assembly 400 that includes the radiation opaque marker 320 on a top of the couch 106. In some aspects, the target 320 may be positioned in the radiation field of the radiation beam 210 on the axis 910 of rotation of the collimator 104 of the gantry 102 of the LINAC 100 for any angle of the gantry 102. In some alternative aspects, the target 320 may be positioned in the radiation field of the radiation beam 210 at the isocenter of the LINAC 100.

In some aspects, the process 1200 may include, for each beam alignment parameter value of a set of beam alignment parameter values, a step 1204 of setting the beam alignment parameter of the LINAC 100 to the beam alignment parameter value. In some aspects, the beam alignment parameter of the LINAC 100 may be, for example and without limitation, an amount of current applied to a bending magnet 204 of the LINAC 100.

In some aspects, the process 1200 may include, for each beam alignment parameter value of the set of beam alignment parameter values, a step 1206 of, with a beam alignment parameter of the LINAC 100 set to the beam alignment parameter value, use a gantry 102 of the LINAC 100 to generate a radiation beam 210.

In some aspects, the process 1200 may include, for each beam alignment parameter value of the set of beam alignment parameter values, a step 1208 of using an imaging device 318 of the LINAC 100 to acquire a radiation transmission image indicative of a radiation field of the radiation beam 210 after passing by a radiation opaque marker 320.

In some aspects, the process 1200 may include, for each beam alignment parameter value of the set of beam alignment parameter values, a step 1210 of determining a location of a beam axis of the radiation beam 210 and a center of a shadow of the radiation opaque marker 320 in the radiation field of the radiation beam 210 based on the radiation transmission image.

In some aspects, determining the location of the beam axis of the radiation beam 210 may include determining a center of the radiation field of the radiation beam 210 based on the radiation transmission image, and the determined location of the beam axis of the radiation beam 210 may be the determined center of the radiation field of the radiation beam 210. In some alternative aspects, (i) determining the location of the beam axis of the radiation beam 210 may include determining a first center of the radiation field of the radiation beam 210 based on the radiation transmission image, (ii) rotating the collimator 104 of the LINAC 100 by 180 degrees, (iii) using the imaging device 318 of the LINAC 100 to acquire a second radiation transmission image indicative of the radiation field of the radiation beam 210 with the collimator 104 rotated by 180 degrees, (iv) determining a second center of the radiation field of the radiation beam 210 based on the second radiation transmission image, and (v) averaging the first and second centers. In some of the alternative aspects, the determined location of the beam axis of the radiation beam 210 may be the average of the first and second centers.

In some aspects, the process 1200 may include, for each beam alignment parameter value of the set of beam alignment parameter values, a step 1212 of determining a target-to-beam-axis distance between the location of the beam axis of the radiation beam 210 and the center of the shadow of the radiation opaque marker 320 in the radiation field of the radiation beam 210.

In some aspects, the process 1200 may include a step 1214 of determining an optimum beam alignment parameter value (e.g., $bp_O$) based on the beam alignment parameter values of the set of beam alignment parameter values and the target-to-beam-axis distances determined with the LINAC 100 set to the beam alignment parameter values of the set of beam alignment parameter values. In some aspects, the optimum beam alignment parameter value may be determined in step 1214 such that a target-to-beam-axis distance between a location of a beam axis of a radiation beam 210 generated by the LINAC 100 with the beam alignment parameter set to the optimum beam alignment parameter value and a center of a shadow of the radiation opaque marker 320 in the radiation field of the radiation beam 210 generated by the LINAC 100 with the beam alignment parameter set to the optimum beam alignment parameter value would be zero (e.g., dx=0).

In some aspects, determining the optimum beam alignment parameter value in step 1214 may include determining a function that models a dependence of the target-to-beam-axis distance on the beam alignment parameter based on the beam alignment parameter values of the set of beam alignment parameter values and the target-to-beam-axis distances determined with the LINAC 100 set to the beam alignment parameter values of the set of beam alignment parameter values. In some aspects, determining the optimum beam alignment parameter value in step 1214 may include using the function to determine a beam alignment parameter value at which a target-to-beam-axis distance would be zero. In some aspects, the function may be a first degree polynomial function. In some aspects, determining the function may include performing a linear least square fit for the target-to-beam-axis distances determined with the LINAC 100 set to the beam alignment parameter values of the set of beam alignment parameter values.

In some aspects, the process 1200 may include a step 1216 of setting the beam alignment parameter of the LINAC 100 to the optimum beam alignment parameter value determined in step 1214 and, with the beam alignment parameter of the LINAC 100 set to the optimum beam alignment parameter value, using the LINAC 100 to generate a radiation beam 210.

In some aspects, the process 1200 may further include repeating steps 1204 through 1214 (and/or step 1216) for each direction that the radiation beam 210 can be aligned.

2.6 LINAC Controller

Figure 13:
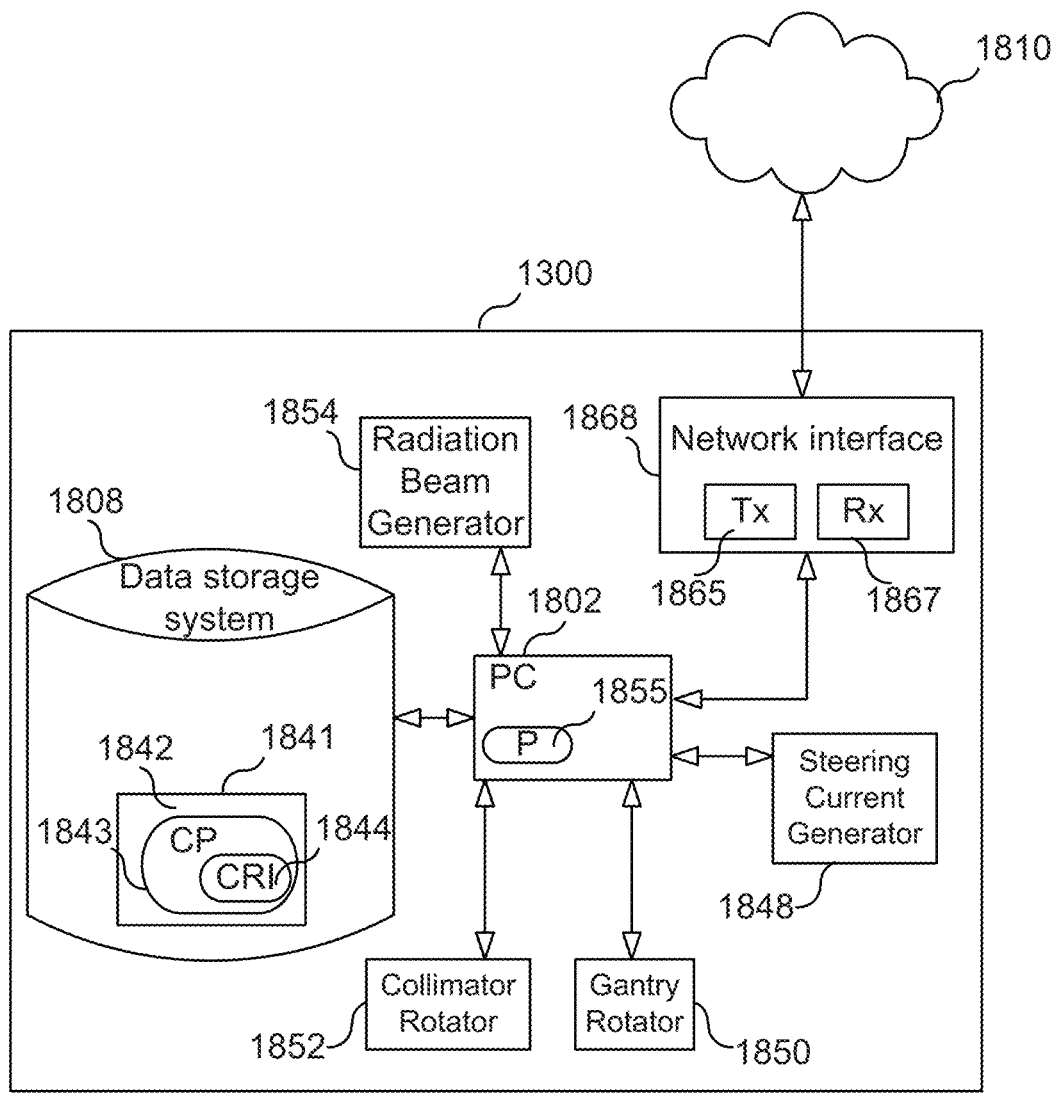
FIG. 13 illustrates a controller of a LINAC according to some aspects.

FIG. 13 is a block diagram of a controller 1300 of a LINAC 100 according to some aspects. As shown in FIG. 13, the controller 1300 may comprise: processing circuitry (PC) 1802, which may include one or more processors (P) 1855 (e.g., one or more general purpose microprocessors and/or one or more other processors, such as an application specific integrated circuit (ASIC), field-programmable gate arrays (FPGAs), and the like), which processors may be co-located in a single housing or in a single data center or may be geographically distributed (i.e., the system may be a distributed computing apparatus); a network interface 1868 comprising a transmitter (Tx) 1865 and a receiver (Rx) 1867 for enabling the controller 1800 to transmit data to and receive data from other nodes connected to a network 1810 (e.g., an Internet Protocol (IP) network) to which network interface 1868 is connected; a steering current generator 1848 configured to supply beam steering currents for the one or more bending magnets 204; a gantry rotator 1850 configured to rotate the gantry 102 about a gantry axis of rotation 808; a collimator rotator 1852 configured to rotate the collimator 104 about a collimator axis of rotation 910; a radiation beam generator 1854 configured to generate an electron beam in the waveguide 202 of the LINAC 100; and a local storage unit (a.k.a., "data storage system") 1808, which may include one or more non-volatile storage devices and/or one or more volatile storage devices. In aspects where PC 1802 includes a programmable processor, a computer program product (CPP) 1841 may be provided. In some aspects, the CPP 1841 may include a computer readable medium (CRM) 1842 storing a computer program (CP) 1843 comprising computer readable instructions (CRI) 1844. In some aspects, the CRM 1842 may be a non-transitory computer readable medium, such as, magnetic media (e.g., a hard disk), optical media, memory devices (e.g., random access memory, flash memory), and the like. In some aspects, the CRI 1844 of computer program 1843 may be configured such that when executed by PC 1802, the CRI causes the LINAC 100 to perform steps described herein (e.g., one or more steps described herein with reference to the flowcharts herein). In other aspects, the controller 1300 may be configured to perform steps described herein without the need for code. That is, for example, the PC 1802 may consist merely of one or more ASICs. Hence, the features of the aspects described herein may be implemented in hardware and/or software.

2.7 Apparatus

Figure 14:
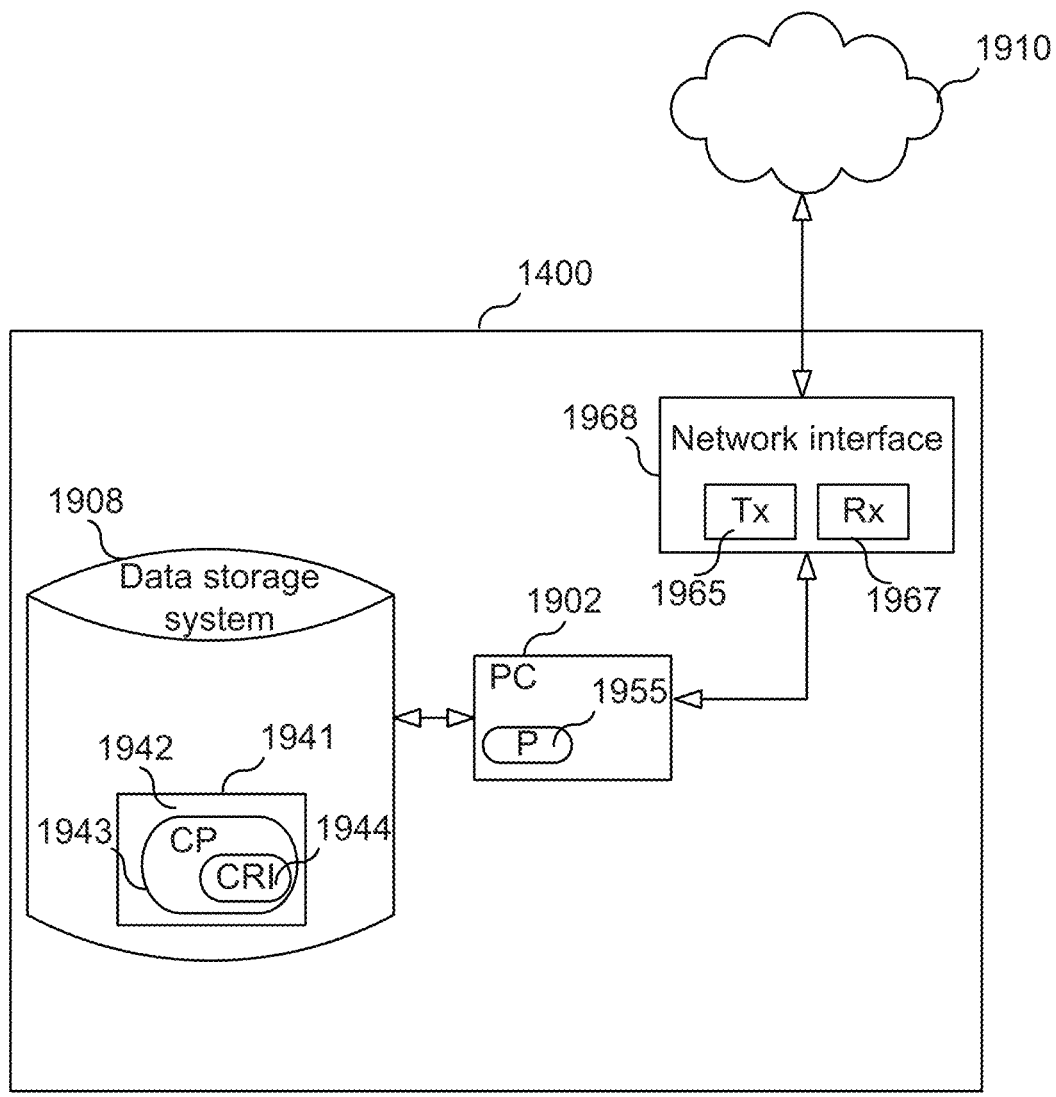
FIG. 14 illustrates an apparatus according to some aspects.

FIG. 14 is a block diagram of an apparatus 1400 according to some aspects. As shown in FIG. 14, the apparatus 1400 may comprise: processing circuitry (PC) 1902, which may include one or more processors (P) 1955 (e.g., one or more general purpose microprocessors and/or one or more other processors, such as an application specific integrated circuit (ASIC), field-programmable gate arrays (FPGAs), and the like), which processors may be co-located in a single housing or in a single data center or may be geographically distributed (i.e., the system may be a distributed computing apparatus); a network interface 1968 comprising a transmitter (Tx) 1965 and a receiver (Rx) 1967 for enabling the apparatus 1900 to transmit data to and receive data from other nodes connected to a network 1910 (e.g., an Internet Protocol (IP) network) to which network interface 1968 is connected; and a local storage unit (a.k.a., "data storage system") 1908, which may include one or more non-volatile storage devices and/or one or more volatile storage devices. In aspects where PC 1902 includes a programmable processor, a computer program product (CPP) 1941 may be provided. In some aspects, the CPP 1941 may include a computer readable medium (CRM) 1942 storing a computer program (CP) 1943 comprising computer readable instructions (CRI) 1944. In some aspects, the CRM 1942 may be a non-transitory computer readable medium, such as, magnetic media (e.g., a hard disk), optical media, memory devices (e.g., random access memory, flash memory), and the like. In some aspects, the CRI 1944 of computer program 1943 may be configured such that when executed by PC 1902, the CRI causes the apparatus 1900 to perform steps described herein (e.g., one or more steps described herein with reference to the flowcharts herein). In other aspects, the apparatus 1900 may be configured to perform steps described herein without the need for code. That is, for example, the PC 1902 may consist merely of one or more ASICs. Hence, the features of the aspects described herein may be implemented in hardware and/or software.

While various embodiments are described herein, it should be understood that they have been presented by way of example only, and not limitation. Thus, the breadth and scope of this disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A method comprising:
for each beam alignment parameter value of a set of beam alignment parameter values:
with a beam alignment parameter of a linear accelerator (LINAC) set to the beam alignment parameter value, using a gantry of the LINAC to generate a radiation beam;
using an imaging device of the LINAC to acquire a radiation transmission image indicative of a radiation field of the radiation beam after passing by a radiation opaque marker;
determining a location of a beam axis of the radiation beam and a center of a shadow of the radiation opaque marker in the radiation field of the radiation beam based on the radiation transmission image; and
determining a target-to-beam-axis distance between the location of the beam axis of the radiation beam and the center of the shadow of the radiation opaque marker in the radiation field of the radiation beam; and
determining an optimum beam alignment parameter value based on the beam alignment parameter values of the set of beam alignment parameter values and the target-to-beam-axis distances determined with the LINAC set to the beam alignment parameter values of the set of beam alignment parameter values.

2. The method of claim 1, further comprising, for each beam alignment parameter value of the set of beam alignment parameter values, setting the beam alignment parameter of the LINAC to the beam alignment parameter value.

3. The method of claim 1, wherein the beam alignment parameter of the LINAC is an amount of current applied to a bending magnet of the LINAC.

4. The method of claim 1, wherein the optimum beam alignment parameter value is determined such that a target-to-beam-axis distance between a location of a beam axis of a radiation beam generated by the LINAC with the beam alignment parameter set to the optimum beam alignment parameter value and a center of a shadow of the radiation opaque marker in the radiation field of the radiation beam generated by the LINAC with the beam alignment parameter set to the optimum beam alignment parameter value would be zero.

5. The method of claim 1, wherein determining the optimum beam alignment parameter value comprises:
determining a function that models a dependence of the target-to-beam-axis distance on the beam alignment parameter based on the beam alignment parameter values of the set of beam alignment parameter values and the target-to-beam-axis distances determined with the LINAC set to the beam alignment parameter values of the set of beam alignment parameter values; and
using the function to determine a beam alignment parameter value at which a target-to-beam-axis distance would be zero.

6. The method of claim 5, wherein the function is a first degree polynomial function.

7. The method of claim 5, wherein determining the function comprises performing a linear least square fit for the target-to-beam-axis distances determined with the LINAC set to the beam alignment parameter values of the set of beam alignment parameter values.

8. The method of claim 1, further comprising:
setting the beam alignment parameter of the LINAC to the optimum beam alignment parameter value; and
with the beam alignment parameter of the LINAC set to the optimum beam alignment parameter value, using the LINAC to generate a radiation beam.

9. The method of claim 1, wherein determining the location of the beam axis of the radiation beam comprises determining a center of the radiation field of the radiation beam based on the radiation transmission image, and the determined location of the beam axis of the radiation beam is the determined center of the radiation field of the radiation beam.

10. The method of claim 1, wherein determining the location of the beam axis of the radiation beam comprises:
determining a first center of the radiation field of the radiation beam based on the radiation transmission image;
rotating a collimator of the LINAC by 180 degrees;
using the imaging device of the LINAC to acquire a second radiation transmission image indicative of the radiation field of the radiation beam with the collimator rotated by 180 degrees;
determining a second center of the radiation field of the radiation beam based on the second radiation transmission image; and
averaging the first and second centers, wherein the determined location of the beam axis of the radiation beam is the average of the first and second centers.

11. The method of claim 1, wherein the radiation opaque marker is positioned in the radiation field of the radiation beam at an axis of rotation of a collimator of the gantry of the LINAC for one or more gantry angles.

12. An apparatus configured to:
for each beam alignment parameter value of a set of beam alignment parameter values:
with a beam alignment parameter of the a linear accelerator (LINAC) set to the beam alignment parameter value, use a gantry of the LINAC to generate a radiation beam;
use an imaging device of the LINAC to acquire a radiation transmission image indicative of a radiation field of the radiation beam after passing by a radiation opaque marker;
determine a location of the beam axis of the radiation beam and a center of a shadow of the radiation opaque marker in the radiation field of the radiation beam based on the radiation transmission image; and
determine a target-to-beam-axis distance between the location of the beam axis of the radiation beam and the center of the shadow of the radiation opaque marker in the radiation field of the radiation beam; and
determine an optimum beam alignment parameter value based on the beam alignment parameter values of the set of beam alignment parameter values and the target-to-beam-axis distances determined with the LINAC set to the beam alignment parameter values of the set of beam alignment parameter values.

13. The apparatus of claim 12, wherein the apparatus is further configured to cause the LINAC to, for each beam alignment parameter value of the set of beam alignment parameter values, set the beam alignment parameter of the LINAC to the beam alignment parameter value.

14. The apparatus of claim 12, wherein the gantry comprises a bending magnet, and the beam alignment parameter of the LINAC is an amount of current applied to the bending magnet.

15. The apparatus of claim 12, wherein the optimum beam alignment parameter value is determined such that a target-to-beam-axis distance between a location of a beam axis of a radiation beam generated by the LINAC with the beam alignment parameter set to the optimum beam alignment parameter value and a center of a shadow of the radiation opaque marker in the radiation field of the radiation beam generated by the LINAC with the beam alignment parameter set to the optimum beam alignment parameter value would be zero.

16. The apparatus of claim 12, wherein the apparatus is configured to, in determining the optimum beam alignment parameter value:
determine a function that models a dependence of the target-to-beam-axis distance on the beam alignment parameter based on the beam alignment parameter values of the set of beam alignment parameter values and the target-to-beam-axis distances determined with the LINAC set to the beam alignment parameter values of the set of beam alignment parameter values; and
use the function to determine a beam alignment parameter value at which a target-to-beam-axis distance would be zero.

17. The apparatus of claim 16, wherein the apparatus is configured to, in determining the function, perform a linear least square fit for the target-to-axis-beam distances determined with the LINAC set to the beam alignment parameter values of the set of beam alignment parameter values.

18. The apparatus of claim 12, wherein the apparatus is further configured to:
set the beam alignment parameter of the LINAC to the optimum beam alignment parameter value; and
with the beam alignment parameter of the LINAC set to the optimum beam alignment parameter value, use the LINAC to generate a radiation beam.

19. The apparatus of claim 12, wherein the gantry comprises a collimator and a bending magnet.

20. The apparatus of claim 12, wherein the radiation opaque marker is positioned in the radiation field of the radiation beam at an axis of rotation of a collimator of the gantry of the LINAC for one or more gantry angles.

* * * * *